US005951601A

United States Patent [19]

Lesinski et al.

[11] Patent Number: 5,951,601
[45] Date of Patent: Sep. 14, 1999

[54] ATTACHING AN IMPLANTABLE HEARING AID MICROACTUATOR

[76] Inventors: S. George Lesinski, 324 Bishopbridge Dr., Cincinnati, Ohio 45225; Armand P. Neukermans; Christopher P. Neukermans, both of 3510 Arbutus Ave., Palo Alto, Calif. 94303

[21] Appl. No.: 08/823,224

[22] Filed: Mar. 24, 1997

Related U.S. Application Data

[60] Provisional application No. 60/014,141, Mar. 25, 1996.

[51] Int. Cl.$^6$ .......... A61F 2/18
[52] U.S. Cl. .......... 623/10
[58] Field of Search .......... 623/10; 607/57, 607/115, 136, 137; 600/25

[56] References Cited

U.S. PATENT DOCUMENTS

| | | |
|---|---|---|
| Re. 31,031 | 9/1982 | Kissiah, Jr. . |
| 1,076,210 | 10/1913 | Kerr et al. . |
| 3,346,704 | 10/1967 | Mahoney . |
| 3,557,775 | 1/1971 | Mahoney . |
| 3,594,514 | 7/1971 | Wingrove . |
| 3,712,962 | 1/1973 | Epley . |
| 3,764,748 | 10/1973 | Branch et al. . |

(List continued on next page.)

FOREIGN PATENT DOCUMENTS

| | | | |
|---|---|---|---|
| 0 076 069 | 4/1983 | European Pat. Off. . | |
| 0 222 509 | 5/1987 | European Pat. Off. | 623/10 |
| 0 242 038 | 10/1987 | European Pat. Off. . | |
| 0 259 906 | 3/1988 | European Pat. Off. . | |
| 0 263 254 | 4/1988 | European Pat. Off. . | |
| 0 563 767 | 10/1993 | European Pat. Off. . | |
| 2688132 | 6/1993 | France . | |
| 28 25 233 | 1/1979 | Germany . | |
| 36 17 118 | 8/1989 | Germany . | |
| 39 18 086 | 9/1990 | Germany . | |
| 1551371 | 3/1990 | U.S.S.R. . | |
| 1440724 | 6/1976 | United Kingdom . | |
| 2176078 | 4/1986 | United Kingdom . | |
| 2188290 | 5/1986 | United Kingdom . | |
| WO 82/01655 | 5/1982 | WIPO | 607/57 |
| WO 90/00040 | 1/1990 | WIPO . | |
| WO 90/07915 | 7/1990 | WIPO . | |

OTHER PUBLICATIONS

Laser in Revision Stapes Surgery, S. George Lesinski, M.D., Janet A. Stein, Head and Neck Surgery, vol. 3, No. 1 (Mar.) 1992, pp. 21–31.

History of Implantable Hearing Aid Development: Review and Analysis, John M. Epley, edited by I. Kaufman Arenberg, Kugler Publications 1991.

Implantable hearing Aid, Arch Otolaryngol Head Neck Surg.—vol. 113, Aug. 1987.

(List continued on next page.)

*Primary Examiner*—David J. Isabella
*Attorney, Agent, or Firm*—Donald E. Schreiber

[57] ABSTRACT

A microactuator (32) of an implantable hearing aid system (10) is secured within a casing (50) implanted into a fenestration (52) that pierces the promontory (18) of the otic capsule bone (31). The casing (50) includes a hollow sleeve (62) that has an outer surface (64) and a first end (66) that is received into the fenestration (52). The sleeve (62) also includes an inner surface (68) adapted to receive a barrel (74) of the microactuator (32). The casing (62) also includes a flange (76) that is integral with the sleeve (62) and projects outward from the outer surface (64) of the sleeve (62) about a second end (78) of the sleeve (62). Various means secure the sleeve (62) within the fenestration (52) such as screwing into the promontory (18) or clamping to the promontory (18). The casing may fasten the microactuator (32) to the casing (50) by a threaded attachment, with screws, with button-and-socket snap fasteners, or with a slotted tongue-and-groove lock. A dummy plug may replace the microactuator (32) should removal become necessary.

23 Claims, 5 Drawing Sheets

U.S. PATENT DOCUMENTS

| | | | |
|---|---|---|---|
| 3,870,832 | 3/1975 | Fredrickson . | |
| 3,882,285 | 5/1975 | Nunley et al. . | |
| 4,078,160 | 3/1978 | Bost . | |
| 4,367,426 | 1/1983 | Kumada et al. . | |
| 4,383,196 | 5/1983 | Perduijn et al. . | |
| 4,419,495 | 12/1983 | Hochmair et al. . | |
| 4,498,461 | 2/1985 | Hakansson . | |
| 4,606,329 | 8/1986 | Hough . | |
| 4,617,913 | 10/1986 | Eddington . | |
| 4,704,126 | 11/1987 | Baswell et al. | 623/10 |
| 4,726,099 | 2/1988 | Card et al. . | |
| 4,729,366 | 3/1988 | Schaefer . | |
| 4,744,792 | 5/1988 | Sander et al. | 623/10 |
| 4,756,312 | 7/1988 | Epley . | |
| 4,817,607 | 4/1989 | Tatge . | |
| 4,817,609 | 4/1989 | Perkins et al. . | |
| 4,850,962 | 7/1989 | Schaefer . | |
| 4,908,509 | 3/1990 | Senturia . | |
| 4,928,264 | 5/1990 | Kahn . | |
| 4,932,405 | 6/1990 | Peters et al. . | |
| 4,943,750 | 7/1990 | Howe et al. . | |
| 4,957,478 | 9/1990 | Maniglia . | |
| 4,985,926 | 1/1991 | Foster . | |
| 4,988,333 | 1/1991 | Engebretson et al. . | |
| 4,999,819 | 3/1991 | Newnham et al. . | |
| 5,015,224 | 5/1991 | Maniglia . | |
| 5,015,225 | 5/1991 | Hough et al. . | |
| 5,033,999 | 7/1991 | Mersky . | |
| 5,047,053 | 9/1991 | Jahn | 623/10 |
| 5,061,282 | 10/1991 | Jacobs . | |
| 5,070,535 | 12/1991 | Hochmair et al. . | |
| 5,085,628 | 2/1992 | Engebretson et al. | 600/25 |
| 5,091,820 | 2/1992 | Iwaya et al. . | |
| 5,095,904 | 3/1992 | Seligman et al. . | |
| 5,176,620 | 1/1993 | Gilman . | |
| 5,180,391 | 1/1993 | Beoni | 623/10 |
| 5,191,559 | 3/1993 | Kahn et al. . | |
| 5,246,455 | 9/1993 | Shikani | 623/10 |
| 5,271,397 | 12/1993 | Seligman et al. | 607/137 |
| 5,276,657 | 1/1994 | Newnham et al. . | |
| 5,277,694 | 1/1994 | Leysieffer et al. | 600/25 |
| 5,282,858 | 2/1994 | Bisch et al. | 623/10 |
| 5,306,299 | 4/1994 | Applebaum | 623/10 |
| 5,318,502 | 6/1994 | Gilman | 600/25 |
| 5,344,387 | 9/1994 | Lupin | 600/25 |
| 5,376,857 | 12/1994 | Takeuchi et al. . | |
| 5,405,388 | 4/1995 | Fox | 623/16 |
| 5,408,534 | 4/1995 | Lenzini et al. . | |
| 5,411,467 | 5/1995 | Hortmann et al. | 600/25 |
| 5,456,654 | 10/1995 | Ball | 600/25 |
| 5,471,721 | 12/1995 | Haertling | 29/25.35 |
| 5,498,226 | 3/1996 | Lenkauskas | 600/25 |
| 5,531,787 | 7/1996 | Lesinski et al. | 623/10 |
| 5,554,096 | 9/1996 | Ball | 600/25 |

OTHER PUBLICATIONS

Implantable Hearing Devices—State of the Art, Anthony J. Maniglia, M.D., Otolaryngologic Clinics of North America, vol. 22, No. 1, Feb. 1989, pp. 175–200.

Laser for Otosclerosis—Which One if Any and Why, S. George Lesinski, M.D., Lasers in Surgery and Medicine 10:448–457 (1990).

Current Status of Electromagnetic Implants Hearing Aids, Richard L. Goode, M.D., Otolaryngologic Clinics of North America, vol. 22, No. 1, Feb. 1989, pp. 201–209.

Microfabrication Techniques for integrated Sensors and Microsystems, K.D. Wise, et al., Science, vol. 254, Nov. 1991, pp. 1335–1341.

Lasers for Otosclerosis, S. George Lesinski, M.D., The Laryngoscope, Supplement No. 46, Jun. 1989, vol. 99, No. 6, Part 2, pp. 1–24.

Homograft Tympanoplasty in Perspective, A Long–Term Clinical–Histologic Study of Formalin–Fixed Tympanic Membranes Used for the Reconstruction of 125 Severly Damaged Middle Ears, s. George Lesinski, M.D., The Laryngoscope, Supp. No. 32—vol. 93, No. 11, Part 2, Nov. 1983, pp. 1–37.

Homograft (Allograft) Tympanoplasty Update, S. George Lesinski, M.D., Laryngoscope, vol. 96, No. 11, Nov. 1986.

Reconstruction Of Hearing When malleus Is Absent: Torp vs. Homograft TMMI.*, Reprint from Laryngoscope, vol. 94, No. 11, Nov. 1984.

"How I Do It"—Otology and Neurotology, Laryngoscope 93: Jun. 1983, pp. 824–825.

Hearing Aids: A Historical and Technical Review, W. F. Carver, Ph.D., Jack Katz, Ph.D., Hnadbook of Clinical Audiology, 1972, pp. 564–576.

ATTACHING AN IMPLANTABLE HEARING AID MICROACTUATOR

CLAIM OF PROVISIONAL APPLICATION RIGHTS

This application claims the benefit of United States Provisional Patent Application Ser. No. 60/014,141 filed on Mar. 25, 1996.

BACKGROUND OF THE INVENTION

1. Field of the Invention

The present invention relates to fully implantable hearing aid system, and more particularly to an apparatus for and method of mounting a microactuator of the fully implantable hearing aid system that permits readily removing the microactuator either permanently or for microactuator replacement.

2. Description of the Prior Art

Patent Cooperation Treaty ("PCT") patent application no. PCT/US96/15087 filed Sep. 19, 1996, entitled "Implantable Hearing Aid" ("the PCT Patent Application") describes an implantable hearing aid which uses a very small implantable microactuator. The PCT Patent Application also discloses a Kynar® microphone which may be physically separated far enough from the implanted microactuator so that no feedback occurs. A PCT patent application no. PCT/US97/002323 entitled "Improved Biocompatible transducers" filed Feb. 14, 1997, ("the Improved Transducers PCT patent application") discloses improved implantable microactuators and microphones that are useful in the fully implantable hearing aid system disclosed in the PCT Patent Application. The fully implantable hearing aid system disclosed in the PCT Patent Application and in the Improved Transducers PCT Patent Application can operate for a period of five years on a set of batteries, and produce sound levels of 110 dB. The fully implantable hearing aid system described in these PCT Patent Applications is extremely compact, sturdy, rugged, and provides significant progress towards addressing problems with presently available hearing aids.

As described in these PCT Patent Applications, the microactuator is implanted into a fenestration that pierces the promontory of the cochlea. The PCT Patent Applications describes securing the microactuator within this fenestration by screwing the microactuator into the bony wall of the promontory. Fixed in that location the microactuator, either directly or indirectly, excites a basilar membrane in contact with the cochlear fluid, and thereby generates sound. However, over time tissue may grow around the microactuator which anchors it firmly in place, but also making its removal very difficult.

The bone at the promontory of the cochlea is extremely hard, and in some instances is only 0.3 to 0.5 mm thick. The bone's hardness impedes attaching the microactuator with barbs. In some instances, forming screw threads into the bone may also prove difficult because of the promontory's thinness.

SUMMARY OF THE INVENTION

An object of the present invention is to facilitate attachment of a microactuator of an implantable hearing aid system to a fenestration formed through a subject's promontory, and to facilitate the microactuator's subsequent removal.

Another object of the present invention is to provide a simple casing for facilitating attachment of a microactuator of an implantable hearing aid system to a fenestration formed through a subject's promontory, and the microactuator's subsequent removal.

Another object of the present invention is to attach a microactuator of an implantable hearing aid system to a fenestration formed through a subject's promontory applying little force to the promontory.

Another object of the present invention is to attach a microactuator of an implantable hearing aid system to a fenestration formed through a subject's promontory without fracturing the promontory.

Another object of the present invention is to removed an implanted microactuator of a hearing aid system from a fenestration formed through a subject's promontory applying little force to the promontory.

Another object of the present invention is to provide an easily implanted casing for attaching a microactuator of an implantable hearing aid system to a fenestration formed through a subject's promontory.

Briefly, the present invention is a casing adapted for implantation into a subject that is receiving an implantable hearing aid system. The casing is implanted into a fenestration that pierces the promontory of the otic capsule bone. The promontory is a projection of the cochlea which is a fluid-filled hearing portion of the inner ear. The casing is adapted for receiving and attaching to the subject either of a microactuator included in the implantable hearing aid system, or of a dummy plug to replace the microactuator should removal of the microactuator become necessary. Upon application of an electric signal to the microactuator, the microactuator stimulates fluid within the inner ear, which stimulation the subject perceives as sound.

A casing for attaching a microactuator of an implantable hearing aid system to a fenestration formed through a subject's promontory in accordance with the present invention includes a sleeve that has an outer surface. During implantation of the casing, a first end of the sleeve is received into the fenestration. Disposed in that location, the outer surface of the sleeve mates with the fenestration for securing the casing within the fenestration. The hollow sleeve includes an inner surface adapted o receive a barrel of the microactuator.

The casing also includes a flange that is integral with the sleeve. The flange projects outward from the outer surface of the sleeve about a second end of the sleeve that is located distal from the first end. The flange, through contact either with a mucosa that covers the promontory or with the promontory itself, limits a depth to which the first end of the sleeve may enter into the fenestration.

A casing in accordance with the present invention may employ various means for securing the sleeve within the fenestration such as screwing into the promontory or clamping to the promontory. Similarly, such a casing may fasten the microactuator to the casing in various ways such as by a threaded attachment, with screws, with button-and-socket snap fasteners, or with a slotted tongue-and-groove lock. A casing in accordance with the present invention may also include a keyway that receives a mating key formed on the barrel of the microactuator for establishing an orientation of the implanted microactuator.

These and other features, objects and advantages will be understood or apparent to those of ordinary skill in the art from the following detailed description of the preferred embodiment as illustrated in the various drawing figures.

DETAILED DESCRIPTION OF THE PREFERRED EMBODIMENT

I The Overall System

Figure 1:
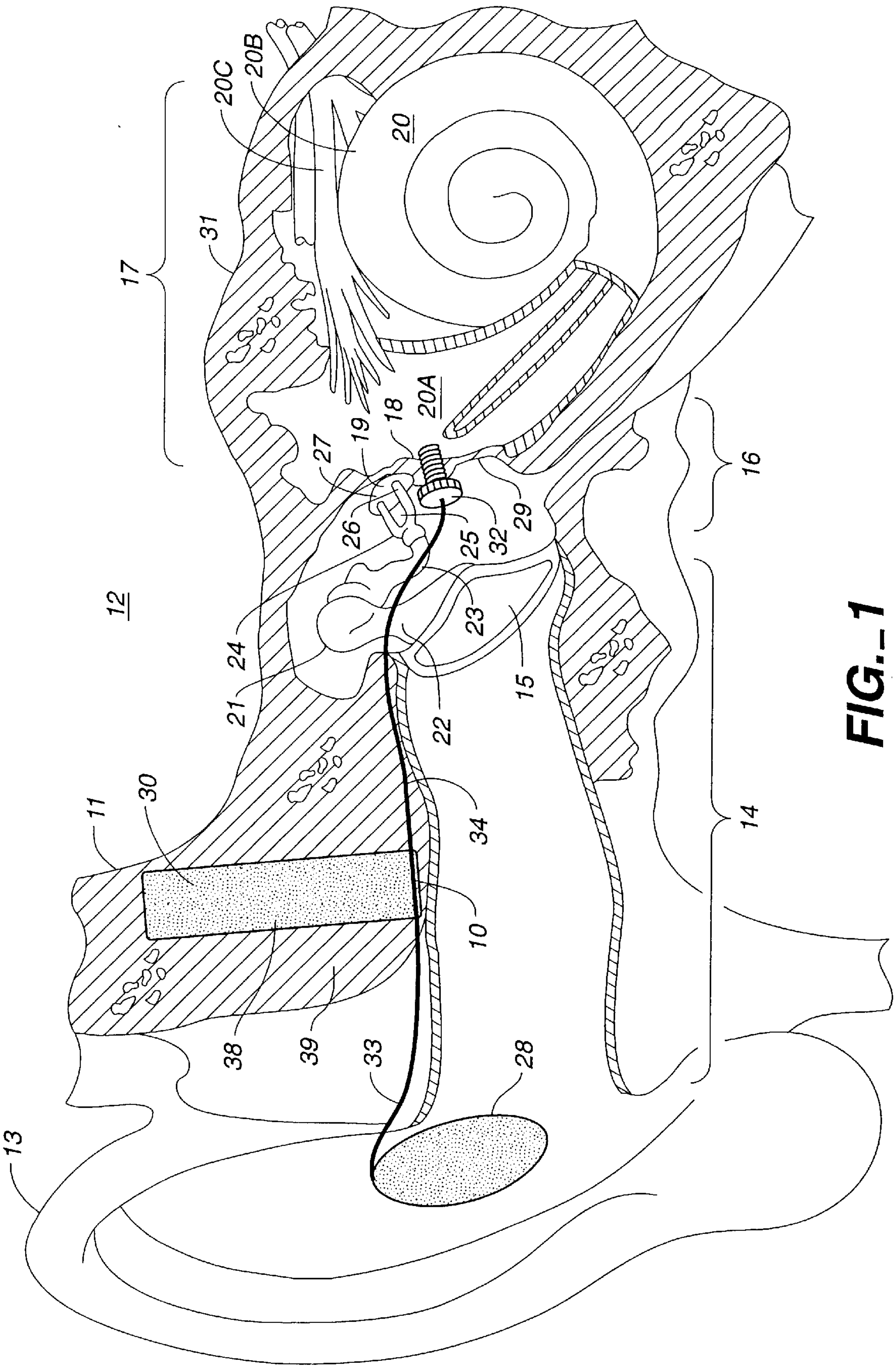
FIG. 1 is a schematic coronal, partial sectional view through a human temporal bone illustrating the external, middle and inner ears, and showing the relative positions of the components of a fully implantable hearing aid system disclosed in the PCT Patent Application.

FIG. 1 illustrates relative locations of components of an implantable hearing aid 10 in accordance with the present invention after implantation in a temporal bone 11 of a human subject 12. FIG. 1 also depicts an external ear 13 located at one end of an external auditory canal 14. An opposite end of the external auditory canal 14 terminates at an ear drum 15. The ear drum 15 mechanically vibrates in response to sound waves that travel through the external auditory canal 14. The ear drum 15 serves as an anatomic barrier between the external auditory canal 14 and a middle ear cavity 16. The ear drum 15 amplifies sound waves by collecting them in a relatively large area and transmitting them to a much smaller area of an oval-shaped window 19. An inner ear 17 is located in the medial aspects of the temporal bone 11. The inner ear 17 is comprised of otic capsule bone 31 containing the semi-circular canals for balance and a cochlea 20 for hearing. A relatively large projection, referred to as the "promontory 18," projects from the otic capsule bone 31 inferior to the oval window 19 which overlies a basal coil of the cochlea 20. A round window 29 is located on the opposite side of the promontory 18 from the oval window 19, and overlies a basal end of the scala tympani.

Three mobile bones (malleus, incus and stapes), referred to as an ossicular chain 21, span the middle ear cavity 16 to connect the ear drum 15 with the inner ear 17 at the oval window 19. The ossicular chain 21 conveys mechanical vibrations of the ear drum 15 to the inner ear 17, mechanically de-amplifying the motion by a factor of 2.2 at 1000 Hz. Vibrations of a stapes footplate 27 in the oval window 19 cause vibrations in perilymph fluid 20*a* contained in scala vestibuli of the cochlea 20. These pressure wave "vibrations" travel through the perilymph fluid 20*a* and endolymph fluid of the cochlea 20 to produce a traveling wave of the basilar membrane. Displacement of the basilar membrane bends "cilia" of the receptor cells 20*b*. The shearing effect of the cilia on the receptor cells 20*b* causes depolarization of the receptor cells 20*b*. Depolarization of the receptor cells 20*b* causes auditory signals to travel in a highly organized manner along auditory nerve fibers 20*c*, through the brainstem to eventually signal the cerebral cortex in the temporal lobe of a brain of the subject 12 to perceive the vibrations as "sound."

The ossicular chain 21 is composed of a malleus 22, an incus 23, and a stapes 24. The stapes 24 is shaped like a "stirrup" with arches 25 and 26 and a stapes footplate 27 which covers the oval window 19. The mobile stapes 24 is supported in the oval window 19 by an annular ligament which attaches the stapes footplate 27 to the solid otic capsule margins of the oval window 19.

FIG. 1 also illustrates the three major components of the hearing aid 10, a microphone 28, a hermetically-sealed signal-processing amplifier 30 which includes a battery not separately depicted in FIG. 1, and microactuator 32. Miniature cables or flexible printed circuits 33 and 34 respectively interconnect the signal-processing amplifier 30 with the microactuator 32, and with the microphone 28. The microphone 28 is mounted below the skin in the auricle, or alternatively in the postauricular area of the external ear 13.

The signal-processing amplifier 30 is implanted subcutaneously behind the external ear 13 within a depression 38 surgically sculpted in a mastoid cortical bone 39 of the subject 12. The signal-processing amplifier 30 receives a signal from the microphone 28 via the miniature cable 33, amplifies and conditions that signal, and then re-transmits the processed signal to the microactuator 32 via the miniature cable 34 implanted below the skin in the external auditory canal 14. The signal-processing amplifier 30 processes the signal received from the microphone 28 to optimally match characteristics of the processed signal to the microactuator 32 to obtain the desired auditory response. The signal-processing amplifier 30 may perform signal processing using either digital or analog signal processing, and may employ both nonlinear and highly complex signal processing.

The microactuator 32 transduces the electrical signal received from the signal-processing amplifier 30 into vibrations that either directly or indirectly mechanically vibrate the perilymph fluid 20*a* in the inner ear 17. As described previously, vibrations in the perilymph fluid 20*a* actuate the receptor cells 20*b* to stimulate the auditory nerve fibers 20*c* which signal the brain of the subject 12 to perceive the mechanical vibrations as sound.

FIG. 1 depicts the relative position of the microphone 28, the signal-processing amplifier 30 and the microactuator 32 with respect to the external ear 13. Even though the signal-processing amplifier 30 is implanted subcutaneously, the subject 12 may control the operation of the hearing aid 10 using techniques analogous to those presently employed for controlling the operation of miniaturized external hearing aids. Both the microphone 28 and the microactuator 32 are so minuscule that their implantation requires little or no destruction of the tissue of the subject 12. Of equal importance, the microphone 28 and the signal-processing amplifier 30 do not interfere with the normal conduction of sound through the ear, and thus will not impair hearing when the hearing aid 10 is turned off or not functioning.

II Threaded Attachment

Figure 2:
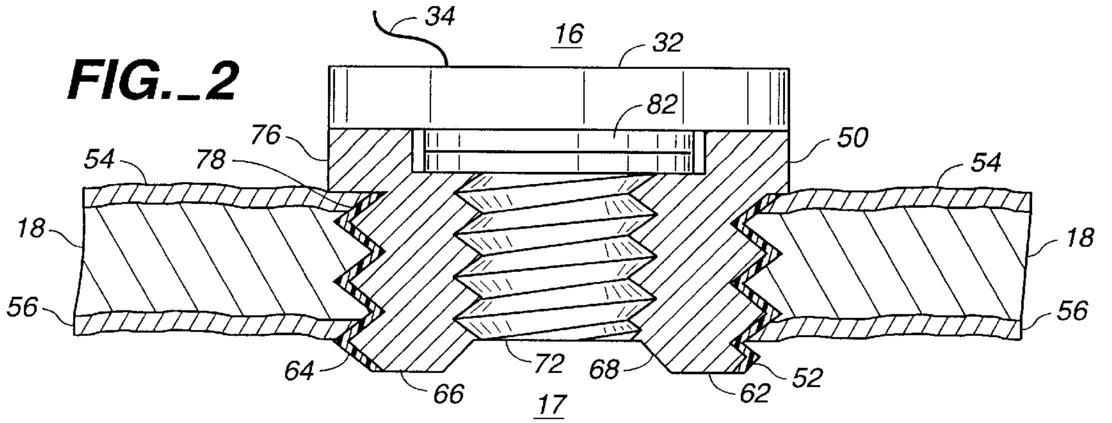
FIG. 2 is a partial cross-sectional elevational view illustrating an externally and internally threaded casing, that includes an integral sleeve and flange, used for attaching an implantable hearing aid's microactuator into a fenestration that pierces the promontory.

FIG. 2 illustrates an embodiment of the present invention for attaching the microactuator 32 to the subject 12 using a casing 50 implanted into a fenestration 52 that pierces the promontory 18 projecting from the otic capsule bone 31. Due to anatomical constraints, the diameter of the fenestration 52 cannot exceed 1.6 mm. As illustrated in FIG. 2, a layer of tissue, identified as mucosa 54, covers that side of the promontory 18 facing the middle ear cavity 16. Another layer of tissue, identified as endothelium 56, covers that side of the promontory 18 facing the inner ear 17. To avoid sensory damage, the fenestration 52 may be formed through the mucosa 54, promontory 18 and endothelium 56 using a low-speed drill (not illustrated in any of the FIGS.) which rotates at a speed below 200 Hz. Alternatively, a pulsed laser beam with appropriate energy parameters may be used for forming the fenestration 52 through the mucosa 54, promontory 18 and endothelium 56. Spectroscopic studies of the human otic capsule bone 31 suggest that the ideal laser wavelength will include those of the excimer laser, Erbium-YAG and C02 lasers. The preceding procedures for forming the fenestration 52 may penetrate the endothelium 56, or the endothelium 56 may remain intact.

The casing 50 includes hollow sleeve 62 having a threaded outer surface 64 which has a first end 66 that is received into the fenestration 52. The hollow sleeve 62 also has an inner surface 68 that receives a barrel 72 of the microactuator 32. The casing 50 also includes a flange 76 that is formed integrally with the sleeve 62, and that projects outward from the outer surface 64 of the sleeve 62 about a second end 78 of the sleeve 62 that is located distal from the first end 66. The flange 76 limits a depth to which the first end 66 of the sleeve 62 may enter into the fenestration 52 through contact between the flange 76 and either the mucosa 54 overlying the promontory 18, or the promontory 18 itself, should the mucosa 54 be removed or forced aside. The casing 50 may be made out of titanium or any suitable bio-compatible material, including Teflon, hydroxyapatite, etc.

To secure the embodiment of the casing 50 depicted in FIG. 2 within the fenestration 52, after initially boring, either with a drill or a laser as described above, the fenestration 52 is threaded with a screw tap (not illustrated in any of the figures). The tap has a relatively coarse pitch, on the order of 2 to 4 turns per mm. To avoid damaging structures within the inner ear 17, the tap must have a very precise length, and have a broad shoulder that contacts the mucosa 54 covering the promontory 18 so the tap does not penetrate into the inner ear 17 more than a fraction of mm. Accordingly, a series of taps may be used successively with all taps having the same pitch but increasingly larger diameter. In this way each successive tap provides a slightly deeper cut into the promontory 18 than the previous tap. After tapping the fenestration 52 to prepare it to receive the casing 50 depicted in FIG. 2, the casing 50 is screwed into the promontory 18 thereby mating the threaded sleeve 62 of the casing 50 with the fenestration 52, and thus securing the casing 50 within the fenestration 52.

As illustrated in FIG. 2, the threaded inner surface 68 of the sleeve 62 has a diameter of approximately 1.3 mm. The threads on inner surface 68 may extend along the entire length of the inner surface 68 from the second end 78 to the first end 66, or only through a fraction of its length. The pitch of threads on the inner surface 68 may be substantially smaller than the pitch of the threads on the outer surface 64. During insertion of the casing 50 into the fenestration 52, to prevent any release of cochlear fluid a dummy plug (not illustrated in any of the figures may fill the inner surface 68.

After the casing 50 has been secured in the fenestration 52, the dummy plug is removed and the barrel 72 of the microactuator 32 is screwed into the inner surface 68. An elastomeric seal 82, which encircles the barrel 72 of the microactuator 32 and is disposed between the microactuator 32 and the casing 50, may be used to make a leak tight seal between the microactuator 32 and the casing 50.

When using a fluidic amplifier microactuator 32 as described in the PCT Patent Application and in the Improved Transducers PCT Patent Application, there exists little restriction on the size of the barrel 72, since the size of the transducer located in the middle ear cavity 16 controls the volume displacement of fluid within the microactuator 32. (The PCT Patent Application, the Improved Transducers PCT Patent Application, and U.S. patent applications Ser. No. 08/532,398 entitled “Implatable Hearing Aid” that was filed Sep. 22, 1995, and Ser. No. 08/801,056 entitled “Improved Biocompatible Transducers” that was filed Feb. 24, 1997, are hereby incorporated by reference as though fully set forth here.) Screwing the microactuator 32 into the casing 50 depicted in FIG. 2 requires rotating the miniature cable 34 which can be cumbersome in practice. Likewise, using the casing 50 depicted in FIG. 2 the angular orientation of the microactuator 32 cannot be set, or even determined, until the casing 50 has been installed.

Figure 3:
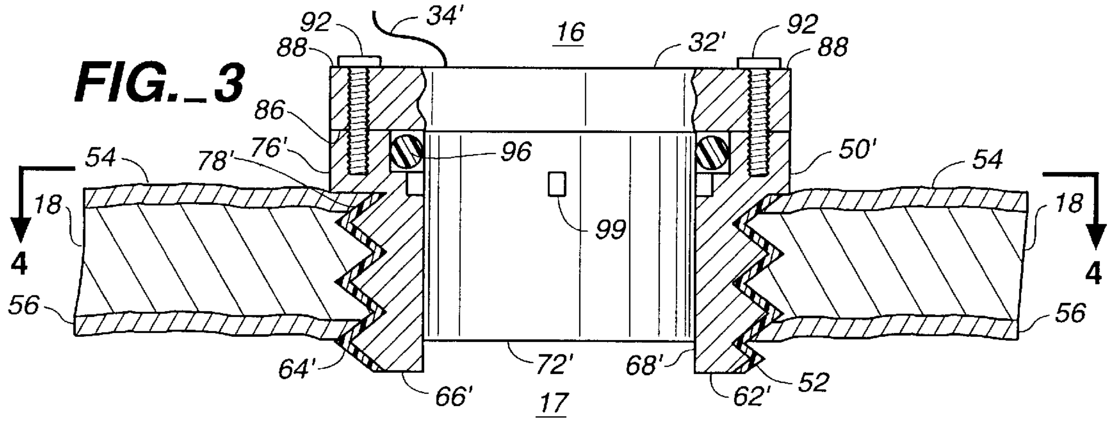
FIG. 3 is a partial cross-sectional elevational view illustrating an alternative embodiment, externally threaded casing and an internal O-ring seal for attaching a microactuator into a fenestration that pierces the promontory.

FIG. 3 illustrates an alternative embodiment of the casing 50. Those elements depicted in FIG. 3 that are common to the casing 50 depicted in FIG. 2 carry the same reference numeral distinguished by a prime (“'”) designation. The embodiment of the casing 50' depicted in FIG. 3 has a smooth, rather than threaded, inner surface 68' of the sleeve 62', and the barrel 72' of the microactuator 32' slips tightly into the externally threaded sleeve 62'. The flange 76' of the casing 50' has threaded apertures 86 formed therein, and adjacent portions of the microactuator 32' are pierced by aligned apertures 88. Screws 92, which respectively extend through the apertures 88 and thread into the threaded apertures 86, secure the microactuator 32' to the casing 50' when the barrel 72' may be received into the sleeve 62'. A small, bio-compatible elastomeric O-ring 96 disposed between the microactuator 32' and the casing 50', may be used to make a leak tight seal between the microactuator 32' and the casing 50'.

Figure 4:
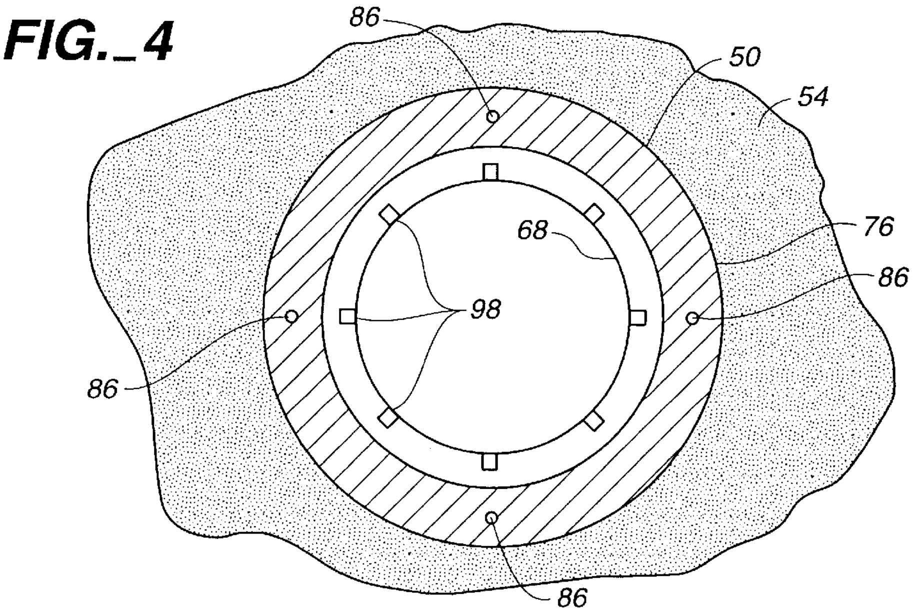
FIG. 4 is a cross-sectional plan view of a casing implanted into a fenestration through the promontory taken along the line 4—4 in FIG. 3.

The cross-sectional view of the casing 50' depicted in FIG. 4 illustrates a keyways 98 notched into the inner surface 68' of the casing 50'. One of the keyways 98 receives a mating key 99, illustrated in FIG. 3, that projects outward from the barrel 72' of the microactuator 32'. Consequently, the microactuator 32' is received into the casing 50' in only a limited number of orientations which are arranged so the apertures 88 that pierce the microactuator 32' align with the threaded apertures 86 formed into the flange 76'. This embodiment of the casing 50' permits orienting the miniature cable 34' to one of a number of desired positions, and also applies a small torque to the casing 50' either when installing or removing the microactuator 32', thereby reducing the possibility of cracking the promontory 18.

III Snap Attachment

Figure 5:
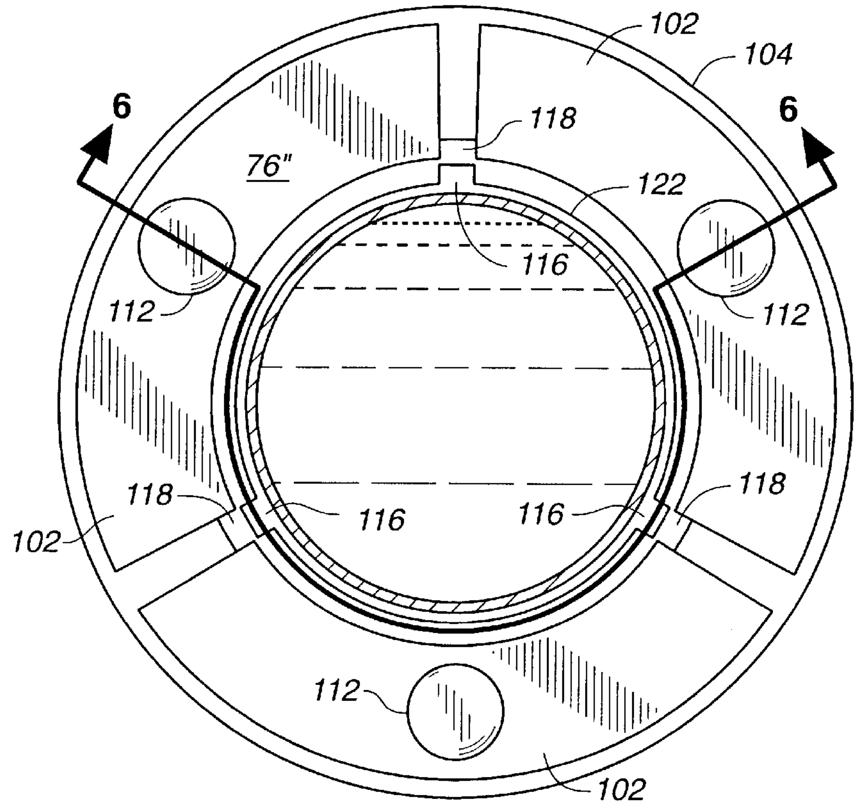
FIG. 5 is a plan view of an alternative embodiment casing that is divided into a plurality of separate, annularly-shaped segments that illustrates reception of a cross-sectional view of the barrel of the microactuator into the casing.
Figure 6:
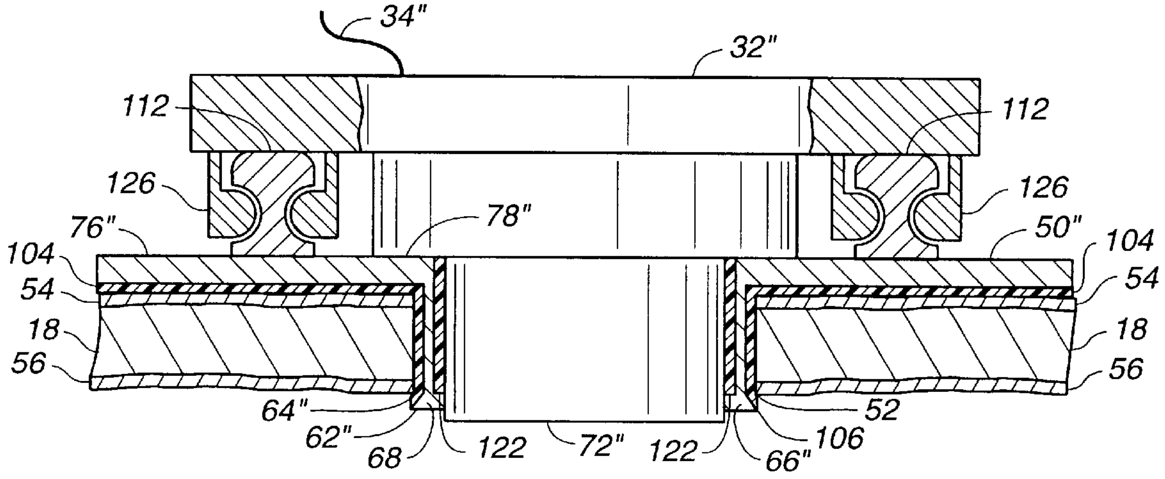
FIG. 6 is a partially sectioned elevational view of the alternative embodiment casing taken along the line 6—6 in FIG. 5 showing reception of the barrel of the microactuator into the casing, and reception of buttons projecting from the flange of the casing into mating sockets on the microactuator.

FIGS. 5 and 6 depict an alternative embodiment of the casing 50. Those elements depicted in FIGS. 5 and 6 that are common to the casing 50 and 50' respectively depicted in FIG. 2 and 3 carry the same reference numeral distinguished by a double prime ("''") designation. The casing 50'' divides the sleeve 62'' and the flange 76'' into a plurality of separate, annularly-shaped segments 102 preferably fabricated from titanium. As illustrated in FIG. 5, the annularly-shaped segments 102 form almost a complete circle. The annularly-shaped segments 102 are attached to and coupled together by a thin, annularly-shaped sheet 104 of an inert and bio-compatible polymeric or elastomeric material. The sheet 104 is approximately 1 to 2 mils thick. Appropriate polymeric materials for the sheet 104 include Teflon®, polyimide, polyvinylidenefluoride ("PVDF") or a similar material. The sheet 104 extends along a surface of the flange 76'' between the flange 76'' and the adjacent mucosa 54, and between the outer surface 64'' of the sleeve 62'' and the fenestration 52. In this way, the sheet 104 seals between the outer surface 64'' of the sleeve 62'' and the promontory 18. While the embodiment of the casing 50'' depicted in FIG. 5 illustrates three annularly-shaped segments 102, a casing 50'' in accordance with this embodiment of the present invention may have other numbers of annularly-shaped segments 102 such as 2 or 4, or even more if desired.

The first end 66'' of the sleeve 62'' is formed with an outwardly-directed, hook-shape to clamp the casing 50'' tightly to the promontory 18. Since the promontory 18 varies in thickness for different subjects 12, during surgery it is desirable to have available for implantation several casings 50'' with differing lengths ranging from 0.3 to 1.0 mm for the sleeve 62''. Typically, the wall of the titanium sleeve 62'' adjacent to the fenestration 52 is approximately 100 to 200 microns thick, and the first end 66 passes through the fenestration 52 which has a diameter of approximately 1.2 to 1.4 mm. After all of the annularly-shaped segments 102 have been inserted into the fenestration 52 so the first end 66'' of the sleeve 62'' is located within the inner ear 17, a tool may be inserted into the sleeve 62 to thereby dilate the casing 50'' and urge the sheet 104 covering the outer surface 64'' of the sleeve 62 into contact with the promontory 18.

As illustrated in FIG. 6, a button 112 projects from a surface of the flange 76'' furthest from the mucosa 54 for each of the annularly-shaped segments 102. Insertion of the casing 50'' into the fenestration 52 may be facilitated by a special tool (not illustrated in any of the figures) which grasps the buttons 112. Because the annularly-shaped segments 102 are secured to each other by the flexible sheet 104, they can be drawn toward each other during insertion into the fenestration 52. Therefore, the insertion tool draws the buttons 112 toward each other thus retracting the hook-shaped first end 66'' to a diameter smaller than that of the fenestration 52. In this way, the casing 50'' can be inserted into a fenestration 52 which is actually slightly smaller in diameter than the hook-shaped first end 66'' of the expanded casing 50''. Upon disengagement of the buttons 112 from the tool, the casing 50'' expands and becomes secured to the promontory 18 surrounding the fenestration 52. Differing from the casing 50 or 50' depicted in FIGS. 2 and 3, the casing 50'' illustrated in FIGS. 6 and 7 may be secured to the promontory 18 at any orientation thereby facilitating subsequent installation of the microactuator 32'' into the casing 50''.

The barrel 72'' of the microactuator 32'' adapted for insertion into the casing 50'' is formed with a slight conical taper (depicted in FIG. 6), and also projecting splines 116 (depicted in FIG. 5) that fit into gaps 118 between the expanded annularly-shaped segments 102. In this way the shape of the sleeve 62'' established by the annularly-shaped segments 102 provides keyways, i.e. the gaps 118, that are adapted to receive mating keys, i.e. the splines 116, formed on the barrel 72'' of the microactuator 32''. The inner surface 68'' of the sleeve 62'' is preferably formed with a conical taper matching that of the barrel 72'' of the microactuator 32''. The barrel 72'' is coated with a thin layer 122 of polymeric material to seal well against the inner surface 68 of the sleeve 62, and against the polymer sheet 104 in the gaps 118 between the annularly-shaped segments 102. The polymeric layer 122 may be provided by a 1–2 mils thick parylene coating.

Due to the tapered shape of the barrel 72'', insertion of the barrel 72'' into the casing 50'' expands the annularly-shaped segments 102 of the sleeve 62'' against the surrounding promontory 18 thereby sealing the casing 50'' and the microactuator 32'' in place. As illustrated in FIG. 6, after insertion of the barrel 72'' into the sleeve 62'' begins, further advancement of the barrel 72'' into the sleeve 62'' also causes circularly-shaped sockets 126 to snap around each of the buttons 112. As illustrated in FIG. 6, each of the sockets 126 includes several slots which permit expansion of the socket 126 as it slips over the head of the mating button 112. The convex radius of the socket 126 which contacts the button 112 is preferably larger than the convex radius of the mating button 112 so the socket 126 is self-centering along the length of the button 112. While hooks, or other types of fasteners might be used to secure the microactuator 32'' to the casing 50'', preferably the mated buttons 112 and sockets 126 hold the microactuator 32 in place against the casing 50''.

A tool may be used for engaging the microactuator 32'' with the casing 50'' which applies no pressure to the promontory 18, but only to the casing 50. If it should become necessary to remove the microactuator 32'' from the casing 50'', another tool can be used which pries the microactuator 32'' loose from the casing 50'' without pulling on the promontory 18.

Figure 7:
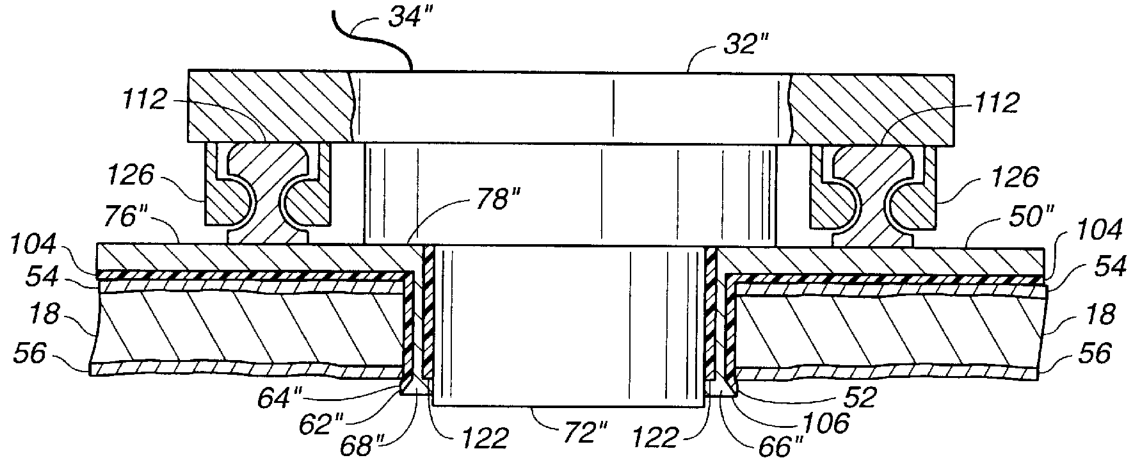
FIG. 7 is a partially sectioned elevational view of the alternative embodiment casing depicted in FIG. 6 that illustrates sockets which provide radially aligned "grooves" for receiving mating buttons that project from the flange of the casing.

To facilitate alignment of the sockets 126 with the buttons 112 and to permit expansion of the annularly-shaped segments 102 as the barrel 72'' mates with the sleeve 62'', the sockets 126 are preferably formed with radially aligned "grooves" as illustrated at the right hand side of FIG. 7. The grooves provide the same transverse cross-section as the sockets 126 depicted at the left-hand side of FIG. 7 and in FIG. 6. However, the radially aligned groove provided by the socket 126 depicted at the right-hand side of FIG. 7 permits radial movement of the buttons 112 with respect to the microactuator 32''. Not all of the sockets 126 of the microactuator 32'' need provide radially aligned grooves. One of the sockets 126 included in the microactuator 32'', as illustrated at the left-hand side of FIG. 7 and in FIG. 6, need not provide a radially aligned groove. If all but one of the sockets 126 of the microactuator 32'' provide radially aligned grooves, alignment with and expansion of the annularly-shaped segments 102 still occurs as the microactuator 32 is pressed into the casing 50''.

Figure 8:
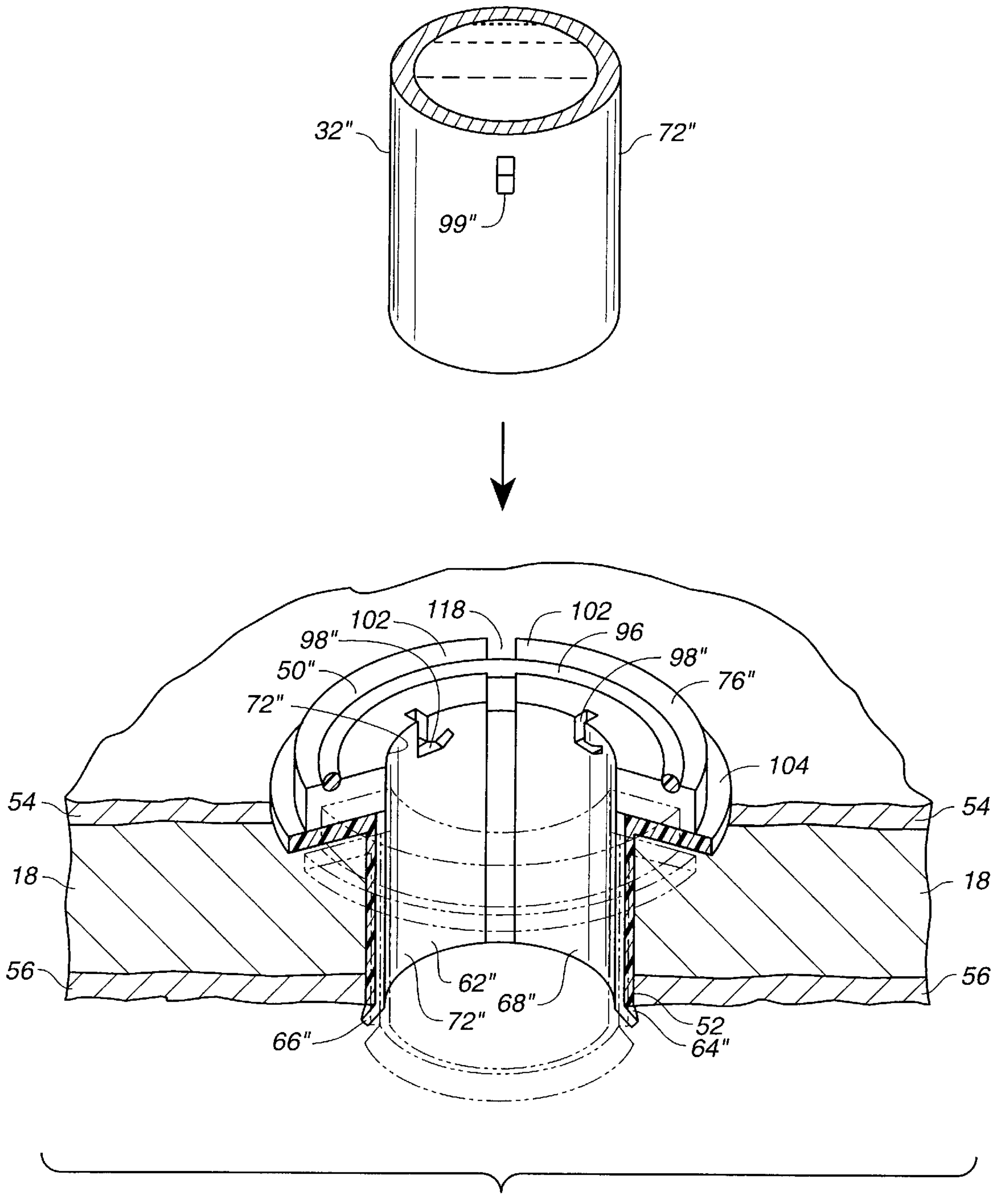
FIG. 8 is a partially sectioned perspective view of the alternative embodiment casing depicted in FIG. 6 that illustrates inserting the microactuator into the casing and securing it there using a keyway formed internally on the casing's sleeve in combination with a key that projects outward from the microactuator's barrel.

FIG. 8 depicts an alternative, tongue-and-groove lock for securing the microactuator 32'' to the casing 50''. Similar to the embodiment depicted in FIGS. 3 and 4, the embodiment depicted in FIG. 8 employs at least two keys 99'' that project outward from the barrel 72'', only one of which is visible in the illustration of FIG. 8. However, the embodiment of FIG. 8 is distinguished from the embodiment of FIGS. 3 and 4 in that the keys 99'' are received into J-shaped keyways 98'' formed into the inner surface 68'' of the sleeve 62''. To secure the microactuator 32'' to the casing 50'', the keys 99'' are aligned with keyways 98'', the barrel 72'' of the microactuator 32" inserted further into the sleeve 62", and then the microactuator 32" is rotated slightly so the keys 99" enter into the ends of the J-shaped keyways 98" furthest from the barrel 72" of the sleeve 62".

Figure 9:
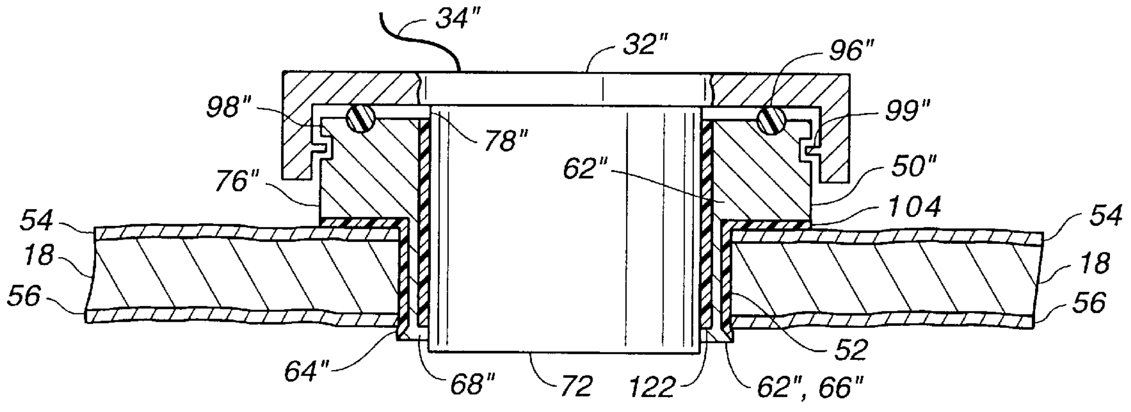
FIG. 9 is a partially sectioned elevational view of the alternative embodiment casing depicted in FIG. 6 that illustrates securing the microactuator to the casing with a keyway formed externally on the casing's flange in combination with a key that projects inward from the microactuator.

FIG. 9 depicts yet another alternative tongue-and-groove lock for securing the microactuator 32" to the casing 50". Similar to the embodiment depicted in FIG. 8, the embodiment depicted in FIG. 9 employs at least two keys 99 that are received into J-shaped keyways 98". However, the embodiment depicted in FIG. 9 is distinguished from the embodiment depicted in FIG. 8 in that the keyways 98" are formed externally on the flange 76" while the keys 99" project inward from an overhanging portion of the microactuator 32" that completely encircles at least a portion of the flange 76".

As described above, forming the fenestration 52 through the promontory 18 may or may not penetrate the endothelium 56. If forming the fenestration 52 penetrates the endothelium 56, then the microactuator 32, 32' or 32", when electrically energized, directly stimulates the fluid within the inner ear 17. If the endothelium 56 remains intact after formation of the fenestration 52, then electrically energizing the microactuator 32, 32' or 32" directly stimulates the endothelium 56, and through the endothelium 56 indirectly stimulates the fluid within the inner ear 17. Under either circumstances, the microactuator 32, 32' or 32" secured within the casing 50, 50' or 50", when electrically energized, stimulates the fluid within the inner ear 17. If for some reason it should become necessary to deactivate the hearing aid 10, then the microactuator 32, 32' or 32" may be removed from the casing 50, 50' or 50", and a dummy plug installed therein. Under such circumstances, because the hearing aid 10 completely bypasses the anatomical hearing structures, e.g. the ear drum 15, the ossicular chain 21 and the stapes footplate 27, the hearing of a subject 12 from which the hearing aid 10 has been removed should return to that existing before its implantation.

Although the present invention has been described in terms of the presently preferred embodiment, it is to be understood that such disclosure is purely illustrative and is not to be interpreted as limiting. For example, parts of the casing 50 may be formed with a shape which differs from that depicted in the FIG. 2 et sec. Such alternative shapes for parts of the casing 50 may be required to avoid any interference with anatomical structures located within the middle ear cavity 16. Analogously, while FIGS. 6 and 7 depict the buttons 112 as projecting from the flange 76" and the sockets 126 as being secured to the microactuator 32", it is readily apparent that the sockets 126 could project from the flange 76" and the button 112 be secured to the microactuator 32". While the present invention discloses mechanically securing the casing 50 within the fenestration 52 that pierces the promontory 18, a casing 50 in accordance with the present invention might also be secured within the fenestration 52 by a suitable bio-compatible adhesive material. Consequently, without departing from the spirit and scope of the invention, various alterations, modifications, and/or alternative applications of the invention will, no doubt, be suggested to those skilled in the art after having read the preceding disclosure. Accordingly, it is intended that the following claims be interpreted as encompassing all alterations, modifications, or alternative applications as fall within the true spirit and scope of the invention.

What is claimed is:

1. A casing and microactuator assembly adapted for implantation into a fenestration that pierces a promontory of an otic capsule bone, the casing and microactuator assembly comprising:

a microactuator; and a casing comprising:

a) a hollow sleeve having an outer surface which has a first end configured to be received into the fenestration, the outer surface of said sleeve being configured to mate with the fenestration for securing the casing within the fenestration, said hollow sleeve also having an inner surface adapted to receive a barrel of the microactuator;

b) a flange integral with said sleeve that projects outward from the outer surface of said sleeve about a second end of said sleeve that is located distal from the first end of said sleeve, said flange having an engagement surface for limiting a depth to which the first end of said sleeve may enter into the fenestration; and c) fastening means for securing the microactuator to the casing when the barrel of the microactuator is received into said sleeve.

2. The casing and microactuator assembly of claim 1 wherein the outer surface of said sleeve is threaded.

3. The casing and microactuator assembly of claim 2 wherein said fastening means includes threads formed on the inner surface of said sleeve that are adapted to engage mating threads on the barrel of the microactuator.

4. The casing and microactuator assembly of claim 3 wherein the casing and the microactuator are shaped to receive an elastomeric seal disposed therebetween.

5. The casing and microactuator assembly of claim 2 wherein said sleeve is shaped to snugly receive the barrel of the microactuator.

6. The casing and microactuator assembly of claim 5 wherein said sleeve is shaped to provide a keyway adapted to receive a mating key formed on the barrel of the microactuator.

7. The casing and microactuator assembly of claim 5 wherein said fastening means includes threaded apertures formed in said flange, the microactuator being pierced by apertures that respectively align with the threaded apertures formed in said flange, said fastening means also including screws each one of which is adapted to extend through one of the apertures that pierce the microactuator and to engage the threaded aperture in the flange that aligns with the aperture through which the screw extends.

8. The casing and microactuator assembly of claim 2 wherein the microactuator is configured to be secured within the casing to directly stimulate fluid within the inner ear.

9. The casing and microactuator assembly of claim 2 wherein the microactuator is configured to be secured within the casing to directly stimulate the endothelium to thereby indirectly stimulate fluid within the inner ear.

10. The casing and microactuator assembly of claim 1 wherein said casing is divided into a plurality of separate, annularly-shaped segments each one of which forms a portion of said sleeve and a portion of said flange.

11. The casing and microactuator assembly of claim 10 wherein the first end of said sleeve is formed with an outwardly-directed, hook-shape for clamping the casing tightly to the promontory upon insertion of said sleeve into the fenestration and expansion of the annularly-shaped segments outward toward the promontory.

12. The casing and microactuator assembly of claim 10 further comprising a sheet of polymeric material that is disposed between said flange and said sleeve of the casing and the promontory when the casing is fastened in the fenestration.

13. The casing and microactuator assembly of claim 12 wherein the annularly-shaped segments forming said sleeve are attached to said sheet of polymeric material.

14. The casing and microactuator assembly of claim 10 wherein the inner surface of said sleeve snugly receives the barrel of the microactuator.

15. The casing and microactuator assembly of claim 14 wherein the barrel of the microactuator is conically-shaped and said sleeve has a conically-shaped inner surface adapted to receive the conically-shaped barrel of the microactuator.

16. The casing and microactuator assembly of claim 15 wherein the barrel of the microactuator includes a key that mates with a keyway provided by said sleeve, and the barrel, including the key, being coated with a polymeric material.

17. The casing and microactuator assembly of claim 10 wherein the fastening means includes buttons that project outward from a face of said flange that is furthest from the promontory when the casing is inserted into the fenestration, said buttons being adapted to be received into and engage mating sockets on the microactuator that are adapted to secure the microactuator to the casing by snapping around said buttons.

18. The casing and microactuator assembly of claim 17 wherein at least one of the sockets is formed as a radially aligned groove adapted to receive and engage one of said buttons along a length of the radially aligned groove.

19. The casing and microactuator assembly of claim 1 wherein the fastening means includes tongue-and-groove lock formed partially on the casing and partially on the microactuator.

20. The casing and microactuator assembly of claim 19 wherein the tongue-and-groove lock includes a keyway formed in the inner surface of said sleeve and a mating key projecting from the barrel of the microactuator.

21. The casing and microactuator assembly of claim 19 wherein the tongue-and-groove lock includes a keyway formed in the inner surface of said flange and a mating key projecting from the microactuator.

22. The casing and microactuator assembly of claim 10 wherein the microactuator is configured to be secured within the casing to penetrate the endothelium, whereby the microactuator, upon being energized, directly stimulates fluid within the inner ear.

23. The casing and microactuator assembly of claim 10 wherein the microactuator is configured to be secured within the casing so as not to penetrate the endothelium, whereby the microactuator, upon being energized, directly stimulates the endothelium to thereby indirectly stimulate fluid within the inner ear.

* * * * *